United States Patent [19]

Sundelin et al.

[11] Patent Number: 4,992,440

[45] Date of Patent: Feb. 12, 1991

[54] SUBSTITUTED 2,3-DIPHENYL-1,2-DIHYDROQUINOXALINES

[75] Inventors: Kurt G. R. Sundelin, Wilmington, Del.; Joseph P. Salanitro, Houston, Tex.; Susan Stackhouse, Hughson, Calif.

[73] Assignee: International Minerals & Chemical Corp., Northbrook, Ill.

[21] Appl. No.: 402,719

[22] Filed: Aug. 30, 1989

Related U.S. Application Data

[62] Division of Ser. No. 260,765, Oct. 21, 1988, Pat. No. 4,886,781.

[51] Int. Cl.$^5$ .................. A61K 31/495; C07D 241/40
[52] U.S. Cl. .................................. 514/248; 514/249; 544/353

[58] Field of Search .................. 514/11, 248, 249; 544/353

[56] References Cited

U.S. PATENT DOCUMENTS 4,886,781 12/1989 Sundelin et al. ................... 514/11

*Primary Examiner*—Stanley J. Friedman
*Assistant Examiner*—Kevin Weddington
*Attorney, Agent, or Firm*—Wendell Ray Guffey; Thomas L. Farquer

[57] ABSTRACT

Novel substituted 2,3-diphenyl-1,2-dihydroquinoxalines are useful for promoting growth and improving feed conversion efficiencies in meat-producing animals. In addition, the novel compounds are useful for controlling coccidiosis in poultry.

8 Claims, No Drawings

SUBSTITUTED 2,3-DIPHENYL-1,2-DIHYDROQUINOXALINES

This application is a division of application Ser. No. 260,765, filed 10/21/88 U.S. Pat. No. 4,886,781.

BACKGROUND OF THE INVENTION

1. Field of the Invention

The present invention relates to compounds which are useful as growth promotants in meat-producing animals and as coccidiostats in poultry and to a method for producing such compounds.

2. Description of the Background Art

For economic reasons, it is desirable to maximize the growth rate and growth efficiency of meat-producing animals during commercial husbandry thereof.

Attempts have been made to increase growth rates of meat-producing animals by administration of various substances including antibiotics (see, e.g., U.S. Pat. No. 4,478,935), resorcylic acid lactone derivatives (see, e.g., U.S. Pat. No. 4,004,978), and quinoxaline derivatives (see, e.g., U.S. Pat. No. 4,012,512). Certain compounds, particularly among the antibiotics, have been found to have both growth-promoting activity and anti-coccidial activity.

There remains a need in the art for compounds and methods for promoting the growth of meat-producing animals and for treatment and prevention of coccidiosis in poultry.

SUMMARY OF THE INVENTION

A compound in accordance with the present invention has the formula:

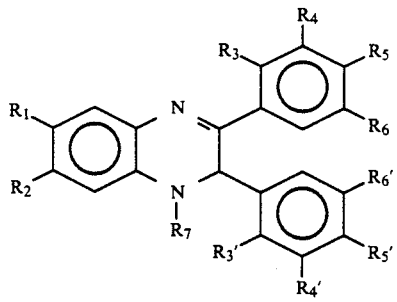

wherein $R_1$ and $R_2$ are independently selected from the group consisting of hydrogen, halogen, lower alkyl and lower alkoxy; $R_3$ and $R_3'$ are independently selected from the group consisting of halogen, hydroxy, lower alkoxy, lower acyloxy and lower alkylcarbonyloxy; $R_4$, $R_4'$, $R_5$, $R_5'$, $R_6$ and $R_6'$ are independently selected from the group consisting of hydrogen, halogen, hydroxy, lower alkyl, lower alkoxy and lower acyloxy; and $R_7$ is hydrogen or lower acyl; or a pharmaceutically acceptable salt thereof. The invention further relates to a method for producing such compounds.

It surprisingly has been found that the novel compounds of the invention are useful for promoting growth in meat-producing animals and for controlling coccidiosis in poultry. Accordingly, the invention further relates to processes for promoting growth in meat-producing animals and for controlling coccidiosis in poultry.

DESCRIPTION OF THE PREFERRED EMBODIMENTS

The present invention relates to novel substituted 2,3-diphenyl-1,2-dihydroquinoxalines of the formula (I)

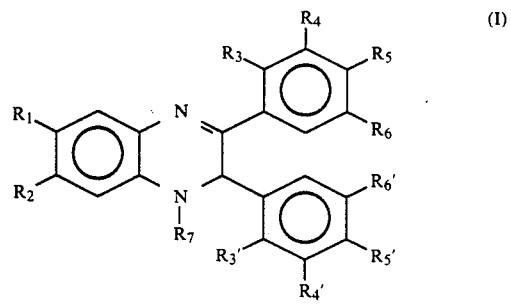

wherein
$R_1$ and $R_2$ are independently selected from the group consisting of hydrogen, halogen, lower alkyl, and lower alkoxy;
$R_3$ and $R_3'$ are independently selected from the group consisting of halogen, hydroxy, lower alkoxy, lower acyloxy, and lower alkoxycarbonyloxy;
$R_4$, $R_4'$, $R_5$, $R_5'$, $R_6$ and $R_6'$ are independently selected from the group consisting of hydrogen, halogen, hydroxy, lower alkyl, lower alkoxy and lower acyloxy; and
$R_7$ is hydrogen or lower acyl; or a pharmaceutically acceptable salt thereof.

In preferred compounds, $R_7$ is hydrogen.

$R_1$ and $R_2$ are preferably independently selected from the group consisting of hydrogen, chloro, bromo, lower alkyl having up to about 5 carbon atoms and lower alkoxy having up to about 5 carbon atoms. In particularly preferred compounds, $R_1$ and $R_2$ are independently selected from the group consisting of hydrogen, chloro, and methoxy.

$R_3$ and $R_3'$ are preferably independently selected from the group consisting of chloro, bromo, hydroxy, lower alkoxy having up to about 5 carbon atoms and lower acyloxy having up to about 5 carbon atoms. In particularly preferred compounds, $R_3$ and $R_3'$ are independently selected from the group consisting of hydroxy, methoxy and acetoxy. Most preferred are those compounds in which $R_3$ and $R_3'$ are each hydroxy.

$R_4$, $R_4'$, $R_5$, $R_5'$, $R_6$ and $R_6'$ are preferably independently selected from the group consisting of hydrogen, chloro, bromo, hydroxy, lower alkyl having up to about 5 carbon atoms, lower alkoxy having up to about 5 carbon atoms and lower acyloxy having up to about 5 carbon atoms. In particularly preferred compounds, $R_4$, $R_4'$, $R_5$, $R_5'$, $R_6$ and $R_6'$ are independently selected from the group consisting of hydrogen, chloro, hydroxy, methyl, methoxy and acetoxy.

The following compounds are examples of preferred substituted 2,3-diphenyl-1,2-dihydroquinoxalines of the present invention:

2,3-di(2-hydroxy-5-chlorophenyl)-6,7-dichloro-1,2-dihydroquinoxaline;

2,3-di(2-hydroxyphenyl)-6,7-dichloro-1,2-dihydroxquinoxaline;

2,3-di(2,4-dichlorophenyl)-6,7-dichloro-1,2-dihydroquinoxaline;

2,3-di(2-hydroxy-5-chlorophenyl)-6-methoxy-1,2-dihydroquinoxaline;

2,3-di(2-hydroxy-5-chlorophenyl)-1,2-dihydroquinoxaline;

2,3-di(2-hydroxy-5-chlorophenyl)-1,2-dihydroquinoxaline;

2,3-di(2,4-dichlorophenyl)-1,2-dihydroquinoxaline 2,3-di(2-hydroxy-5-chlorophenyl)-6,7-dimethyl-1,2-dihydroquinoxaline;

2,3-di(2-hydroxy-4-methoxyphenyl)-6,7-dimethyl-1,2-dihydroquinoxaline;

2,3-di(2-acetoxy-5-chlorophenyl)-6,7-dimethyl-1,2-dihydroquinoxaline;

1-acetyl-2,3-di(2-acetoxy-5-chlorophenyl)-6,7-dichloro-1,2-dihydroquinoxaline;

2,3-di(2-ethoxycarbonyloxy-5-chlorophenyl)-6,7-dichloro-1,2-dihydroquinoxaline;

2,3-di(2-hydroxy-3,5-dibromophenyl)-6,7-dimethyl-1,2-dihydroquinoxaline;

1-acetyl-2-(2-acetoxy-3,5-dibromophenyl)-3-(2-hydroxy-3,5-dibromophenyl)-6,7-dimethyl-1,2-dihydroquinoxaline; and 1-acetyl-2-(2-acetoxy-5-chlorophenyl)-3-(2-hydroxy-5-chlorophenyl)-6,7-dichloro-1,2-dihydroquinoxaline.

The compounds of this invention can be prepared by a unique azabenzoin cyclization condensation reaction.

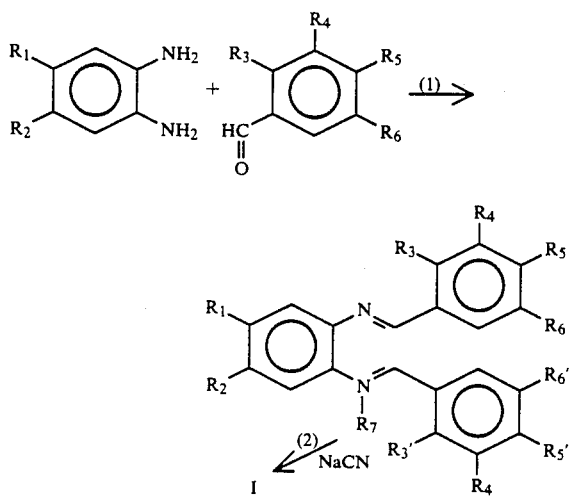

Reaction 1 has been found to proceed to substantial completion under mild reaction conditions. For example, upon heating an ethanolic solution of the phenylenediamine derivative and the benzaldehyde derivative (in a 1:2 molar ratio) to a temperature of about 50°–70° C, substantially complete reaction to the dibenzylidene compound occurs within a few hours to a few days.

The azabenzoin cyclization condensation reaction (2) produces the final product in good yield under relatively mild conditions. Treatment of the dibenzylidene compound with a molar excess of sodium cyanide in a polar organic solvent readily produces the desired product. The reaction temperature may vary, and advantageously ranges from about 0° C to about 30° C.

The compounds of the present invention exhibit a variety of useful biological activities. For example, the compounds have been found useful for increasing the rate of growth or feed conversion efficiencies in meat-producing animals. Perhaps related to this ability to improve weight gain and feed efficiency is the bactericidal activity of the compounds. Certain of the compounds of this invention exhibit potent bactericidal effects on anaerobic bacteria. In general, the compounds have not been found effective against aerobic bacteria. The bactericidal activities of these compounds are complementary to those of many common antibiotics, such as penicillin, tylosin, bacitracin, kanamycin, gentamicin, chlorotetracycline, lincomycin, polymyxin, erythromycin, and the like. It is therefore contemplated that by administering the compounds of the present invention in combination with such conventional antibiotics, a broader spectrum of bactericidal effect can be achieved, with a concomittant improvement in weight gains and feed efficiencies in meat-producing animals.

The present compounds also possess anticoccidial activities. Such compounds can, therefore, be administered in effective amounts to poultry, particularly chickens and turkeys, to control coccidiosis. The compounds can be administered to animals exposed to or susceptible to coccidiosis in prophylactic amounts and can be administered to animals infected with the disease in therapeutic amounts.

The present compounds are generally administered in the form of solutions, suspensions, powders, tablets, capsules, and the like. Preferably, the compounds are incorporated into an animal feed or feed supplement (premix). Alternatively, the compounds may be supplied to animals via their drinking water. When incorporated into a feed supplement, the active compounds can be mixed with conventional feed ingredients, such as calcium phosphate, meat and bone meals, various vitamin and trace mineral compositions, salt, and the like. Such feed supplements are formulated for convenient blending with grain and other components of animal feeds to provide the desired concentration of the active ingredient in the feed.

When used for promoting growth in meat-producing animals, effective amounts can range from about 10 to about 200 milligrams per kilogram of feed. When used for promoting growth in birds, such as turkeys and chickens, the compounds are generally administered in effective amounts which can range from about 10 to about 100 milligrams per kilogram of feed. When used for promoting the rate of growth or improving feed conversion efficiencies in meat producing animals such as cattle, sheep, and swine, dosages ranging from about 10 to about 200 milligrams per kilograms of feed.

For the prophylactic control of coccidiosis in birds, such as chickens and turkeys, the active compounds are administered in coccidiosis-controlling amounts which generally range from about 0.1 to about 50 milligrams per kilogram of feed. For the therapeutic treatment of birds infected with coccidial parasites, dosages range from about 10 to about 100 milligram per kilogram of feed.

The concentration of the present compounds in animal feeds will vary greatly depending upon the species receiving the feed as well as the purpose for administering the compound. As an additive for chicken and turkey feeds, the compounds advantageously achieve the effects of promoting growth and improving feed conversion efficiencies as well as controlling coccidiosis. The concentration of the ingredient in a feed supplement or premix will be adjusted such that the desired concentration of the active compound in the feed will be obtained.

For use in controlling coccidiosis, it is also contemplated that the present compounds can be administered in combination with other cocciodiostats. In particular, it is contemplated that combinations of the present compounds with polyether antibiotics, such as monensin, lasalocid, and lysocellin, can be used.

The invention is further illustrated by the following examples which are not intended to be limiting.

EXAMPLE 1

N,N'-Di(2-hydroxy-5-chlorobenzylidene)-4,5-dichloro-1,2-diaminobenzene

A slurry of 177.0 g (1.0 mole) of 4,5-dichloro-o-phenylenediamine in 750 ml. ethanol was added to a warm near solution of 313.1 g (2.0 mole) of 5-chlorosalicylaldehyde in 2250 ml. of ethanol with mechanical stirring in a 5000 ml, 3-neck flask. A brown solution formed, and a light brown solid began to precipitate after 10–15 minutes. Stirring at room temperature was continued for six days. Thin-layer chromatography indicated that the reaction was substantially complete at the end of six days.

The mixture was filtered and the resulting solid was washed with ethanol and then diethylether, yielding 381.6 g. The product melted at 234°–237° C, then solidified at 239°–240° and did not re-melt until 257°–259° C at which point it slowly decomposed. Elemental analysis was as follows:

|   | Calc. | Found |
|---|-------|-------|
| C | 52.9% | 52.6% |
| H | 2.7   | 2.6   |
| N | 6.2   | 6.3   |
| Cl| 31.2  | 31.2  |

2,3-Di(2-hydroxy-5-chlorophenyl)-6-7-dichloro-1,2-dihydroquinoxaline

To 68.1 g (0.15 mole) of N,N'-di(2-hydroxy-5-chlorobenzylidene)-4,5-dichloro-1,2-diaminobenzene in 150 ml. of dimethylsulfoxide was added 8.1 g. (0.165 mole) of freshly ground sodium cyanide while mechanically stirring in an ice bath under a nitrogen blanket. The thick mixture became homogeneous and darkened. The ice bath was allowed to melt and reach room temperature, and stirring was continued for two days. The resulting dark, homogeneous oil was poured into 9.9 g (0.165 mole) of glacial acetic acid in 1500 ml. of water while stirring. A voluminous solid formed which was removed by filtration, washed with water, slightly air dried, then dried in vacuo at 50° C to 60° C overnight. The solid was treated on a steam bath with acetonitrile to yield a characteristic orange solid. Forty grams of this solid were recovered by filtration. The resulting product melted at 268°–272° C, and the following elemental analysis was obtained:

|   | Calc. | Found |
|---|-------|-------|
| C | 52.9% | 51.6% |
| H | 2.7   | 2.7   |
| N | 6.2   | 5.8   |
| Cl| 31.2  | 30.2  |

EXAMPLES 2–14

The procedures of Example 1 were repeated in all essential details, substituting the appropriate starting materials, to produce the following compounds:

| Example | Compound |
|---------|----------|
| 2  | 2,3-di(2-hydroxyphenyl)-6,7-dichloro-1,2-dihydroquinoxaline; |
| 3  | 2,3-di(2,4-dichlorophenyl)-6,7-dichloro-1,2-dihydroquinoxaline; |
| 4  | 2,3-di(2-hydroxy-5-chlorophenyl)-6-methoxy-1,2-dihydroquinoxaline; |
| 5  | 2,3-di(2-hydroxy-5-chlorophenyl)-1,2-dihydroquinoxaline; |
| 6  | 2,3-di(2,4-dichlorophenyl)-1,2-dihydroquinoxaline |
| 7  | 2,3-di(2-hydroxy-5-chlorophenyl)-6,7-dimethyl-1,2-dihydroquinoxaline; |
| 8  | 2,3-di(2-hydroxy-4-methoxyphenyl)-6,7-dimethyl-1,2-dihydroquinoxaline; |
| 9  | 2,3-di(2-acetoxy-5-chlorophenyl)-6,7-dimethyl-1,2-dihydroquinoxaline; |
| 10 | 1-acetyl-2,3-di(2-acetoxy-5-chlorophenyl)-6,7-dichloro-1,2-dihydroquinoxaline; |
| 11 | 2,3-di(2-ethoxycarbonyloxy-5-chlorophenyl)-6,7-dichloro-1,2-dihydroquinoxaline; |
| 12 | 2,3-di(2-hydroxy-3,5-dibromophenyl)-6,7-dimethyl-1,2-dihydroquinoxaline; |
| 13 | 1-acetyl-2-(2-acetoxy-3,5-dibromophenyl)-3-(2-hydroxy-3,5-dibromophenyl)-6,7-dimethyl-1,2-dihydroquinoxaline; and |
| 14 | 1-acetyl-2-(2-acetoxy-5-chlorophenyl)-3-(2-hydroxy-5-chlorophenyl)-6,7-dichloro-1,2-dihydroquinoxaline. |

EXAMPLE 15

The compound produced by the procedures of Example 1 was tested for antimicrobial activity against several bacteria. The test compound was compared to several known antibiotics which are currently used in animal health and nutrition applications. The comparisons were made at test compound concentrations of 64 $\mu$g/ml and 6.4 $\mu$g/ml.

The procedures for preparing and testing test compounds at 64 $\mu$g/ml and 6.4 $\mu$g/ml for growth inhibition using test organisms were as follows.

About 32 milligrams of test compound were weighed out and dissolved in 50/50 (v/v) acetone/dimethylsulfoxide (DMSO) to a test compound concentration of 6400 $\mu$g/ml.

Solutions of test compound then were prepared as follows for the following strains: *Salmonella typhimurium* (S.T.), antibiotic resistant *E. coli* (E.C. 324), *E. coli* strain 046 (E.C. 046), Streptococcus sp. 1 X C15 (Strep C15), Streptococcus sp. 1 X A7 (Strep A7) and *Clostridium perfringens* (Cp). For the strains listed above, 0.1 milliliter of 6400 $\mu$g/ml test compound solution prepared as above was added to 10 ml sterile Modified Columbia Broth (MCB) medium containing 3.5 grams Columbia Broth (Difco), 0.25 grams glucose, 2.5 grams yeast extract (Difco), and 0.05 grams cystein-HCl, per 100 ml distilled water to give a test compound concentration of 64 $\mu$g/ml. The 6.4 $\mu$g/ml test solution was formed from this 64 $\mu$g/ml solution by taking 1 ml of the 64 $\mu$g/ml test compound solution and adding 9 ml MCB medium.

For *Bacteroides fragilis* (Bf) 64 $\mu$g/ml solutions of test compound were made by adding 0.05 ml of 6400 $\mu$g/ml solutions of test compound (as prepared above) to 5 ml of MCB medium. For this strain, 6.4 $\mu$g/ml solutions of test compound were made by adding 0.2 ml of 6400 $\mu$g/ml test solutions as prepared above to 1.8 ml of 50/50 acetone/DMSO, and from this mixture taking 0.05 ml and adding thereto 5 ml MCB medium.

For preparing test solutions of antibiotics, the above procedure differed only in that the antibiotics were diluted initially in sterile distilled water rather than 50/50 acetone/DMSO.

During testing with strains S.T.; E.C. 324; E.C. 046; Strep C15; Strep A7 and Cp, test solutions containing 64 µg/ml or 6.4 µg/ml test compound were dispensed aseptically to Costar TM plates at 0.9 ml test solution/well.

For strains S.T. and E.C. 046, each test well was inoculated with one drop of strain culture grown for 24 hours at 37° C. in MCB medium.

For strains C15, A7 and Cp, each test well was inoculated with 0.1 ml strain culture grown for 24 hours at 37° C. in MCB medium.

All of the test plates were incubated for 6 hours at 37° C. Plates containing organisms S.T., E.C. 324, E.C. 046, Strep C15 and Strep A7 were incubated aerobically, and plates with organism Cp were incubated anaerobically in gas-packed anaerobic jars.

For tests at 64 µg/ml and 6.4 µg/ml against *Bacteroides fragilis* (Bf), vials were inoculated with 0.1 ml of Bf culture (MCB) grown for 24 hours at 37° C. The inoculated vials then were incubated anaerobically at 37° C. for 6 hours.

For all the tests after 6 hours incubation following inoculation, visual culture turbidity was recorded for the plate wells and vials. Growth was scored for each test organism in the presence of a compound when compared against uninoculated and inoculated controls.

The results of this test are shown in Table 1 below, and demonstrate that the antimicrobial profile complements that of several other well-known antibiotics. In particular, the compound of Example 1 possessed activity against both anaerobic microorganisms. In Table 1, "+" indicates that the bacterium grew in the presence of the test compound and "−" indicates no growth (i.e., inhibition).

TABLE I

| Organism* Compound | Gram Neg. | | | Gram. Pos. | | Anaerobic | |
|---|---|---|---|---|---|---|---|
| | S.T. | E.C. 324 | E.C. 046 | Strep C15 | Strep A7 | Cp | Bf |
| (64 ppm) | | | | | | | |
| Penicillin | − | − | − | − | − | + | − |
| Bacitracin | + | + | + | − | − | − | − |
| Tylosin | + | + | + | − | − | − | − |
| Gentamicin | − | − | − | − | − | + | − |
| Chlortetracycline | − | − | − | − | − | + | − |
| Kanamycin | − | − | + | − | − | + | − |
| Lincomycin | + | + | + | − | − | + | − |
| Polymyxin | − | − | − | − | − | + | − |
| Erythromycin | − | + | − | − | − | + | − |
| Compound of Ex. 1 | + | + | + | + | + | − | − |
| (6.4 ppm) | | | | | | | |
| Penicillin | + | + | + | − | − | + | + |
| Bacitracin | + | + | + | − | − | + | − |
| Tylosin | + | + | + | − | − | + | − |
| Gentamicin | − | + | + | − | − | + | − |
| Chlortetracycline | − | + | + | − | − | + | + |
| Kanamycin | + | + | + | − | − | + | − |
| Lincomycin | + | + | + | − | − | + | − |
| Polymyxin | − | − | − | − | + | + | + |
| Erthromycin | + | + | + | − | − | + | + |
| Compound of Ex. 1 | + | + | + | + | + | − | − |

*S.T. = *Salmonella typhimurium*; E.C. 324 = *E. coli* antibiotic resistant; E.C. 046 = *E. coli* 046; Strep C15 = Streptococcus sp. (1 × C15); Strep A7 = Streptococcus sp. (1 × A7); Cp = *Clostridium perfringens*; Bf = *Bacteroides fragilis*.

EXAMPLE 16

The compound prepared by the procedures of Example 1 was tested for its ability to promote growth or improve feed utilization in chicks compared to the activities of several other well-known antibiotics listed in Table 2.

In this trial, one-day-old broiler cockerels (20 birds/pen, 4 pens/treatment) were fed a broiler ration containing 0, 50 or 75 ppm test compound. The approximate analysis of the broiler ration was 24.2 weight percent protein, 8.2 weight percent fat, 2.7 weight percent fiber, 5.7 weight percent ash, 10.0 weight percent moisture, 49.2 percent nitrogen-free energy, 1.22 percent calcium and 0.58 percent phosphorus. The broiler ration was purchased from Halloran Research Farm, Modesto, Calif. This feed, formulated as a mash, was used throughout the 8-week experimental period. Feed was placed into adjustable circular feeding troughs and "shaken down" and replenished daily as needed. Feed spillage was minimized during the trial by appropriately elevating the troughs weekly.

Water was provided without restriction by means of trigger-sensitive watering cups (one cup/pen).

During the trial, animals were weighed as an entire pen and the number of surviving birds noted at each weighing. Feed consumption also was determined on pen basis and was estimated from the amounts of feed consumed and remaining in a pen.

For statistical analysis, the pen data was converted to a "per bird basis." Feed efficiency was evaluated by analyzing cumulative weight gain adjusted by analysis of covariance to a constant cumulative feed consumption.

The results of this test are shown in Table 2 below. The compound of Example 1 was found to improve both weight gain and feed efficiency. Four sets of experiments were conducted. Each set of experiments included an unmedicated control, and the response was normalized to the value for the control.

TABLE 2

| Compound | Conc. (ppm) | weight gain (% better or worse than control) | feed efficiency (% better or worse than control) |
|---|---|---|---|
| 1. Control | 0 | 0 | 0 |
| Penicillin | 75 | 20 | 5.5 |
| Bacitracin | 75 | 25 | 19 |
| Lincomycin | 75 | 20 | 12 |
| 2. Control | 0 | 0 | 0 |
| Penicillin | 50 | 40 | 32 |
| Bacitracin | 50 | 40 | 32 |
| 3. Control | 0 | 0 | 0 |
| Penicillin | 50 | 35 | 13 |
| Gentamicin | 50 | 32 | 15 |
| 4. Control | 0 | 0 | 0 |
| Penicillin | 50 | 19 | 11 |
| Kanamycin | 50 | 14 | 19 |
| Polymyxin | 50 | −3 | 6 |
| 5. Control | 0 | 0 | 0 |
| Penicillin | 50 | 50 | 21 |
| Compound of Ex. 1 | 75 | 6 | 13 |

EXAMPLE 17

Several of the compounds described in the preceding examples were tested for anticoccidial activity.

In this trial, a reservoir of coccidial oocysts was established by maintaining 300 chicks without previous exposure to either coccidia or anticoccidial drugs, in brooders or battery cages in a coccidia-free room on drug-free feed with water ad libitum.

At 3 weeks of age, chicks were transferred to another building and inoculated per os with 50,000 to 100,000 sporulated oocysts of Eimeria tenella Eli Lilly Strain 65 (Lilly 65). These birds were maintained in batteries with the same feed and water ad libitum.

Fecal pans were examined daily for blood beginning 4 or 5 days post-inoculation. Mortalities were recorded and dead birds incinerated.

One week after inoculation birds were fasted for 18 hours and sacrificed by carbon dioxide asphyxiation. Cecal pouches were removed, and their contents, primarily oocysts and blood, scraped into a glass pan containing distilled water.

The cecal contents/water mixture was homogenized for 1 minute with an Oster TM blender, and the homogenate plus washes placed in a 1000 ml flask. Pepsin (Fisher Scientific Company, P-35, purified powder) was added at 2 mg/ml, the pH adjusted to 1.8-2.0, and the flask placed in a water bath at 37° C. When the oocysts had dissociated from each other and accompanying debris as determined by periodic microscopic examination (1-2 hours), the pH was brought to 8.0 with 10N NaOH and the contents poured into a large flask.

Oocyst preparations were diluted with 3 volumes of distilled water and stored overnight at 3°-5° C. On the following morning, the water was siphoned off to within 1 inch of the residue in the flask, and the remaining contents placed in 250 ml centrifuge bottles.

Oocysts and debris were sedimented by centrifugation (1000 rpm/10 min.). The supernatant and dark debris were siphoned off leaving the greyish oocysts at the bottom of the centrifuge bottles.

Oocysts were transferred in about 20 ml distilled water to 40 ml conical centrifuge tubes along with 2-3 rinses of the centrifuge bottles. Tubes were centrifuged at 1200 rpm/10 min. Again, the water and dark debris were siphoned off.

While in centrifuge tubes pelleted oocysts were washed several times with distilled water to remove debris. Washed oocysts were resuspended in distilled water and transferred to a 500 ml flask. After the addition of $KCr_2O_7$ to 0.5%, the flask was placed in a 30° C water bath and bubbled vigorously with air for 3-5 days to permit sporulation.

When microscopic examination indicated about 90% sporulation of oocysts, approximately 50 ml of the suspension was set aside for inoculation of chicks at a future date. The remaining oocysts were harvested by centrifugation (1000 rpm/10 min.). Supernatants were discarded, and 10-15 ml of commercial Clorox TM (5.25% sodium hypochlorite) was added to each centrifuge tube. Fifteen minutes later tubes were centrifuged (1000 rpm/5 min.) to sediment unsporulated oocysts and debris. The top 10 ml containing the sporulated oocysts (less dense than their unsporulated counterparts because of expansion during Clorox TM treatment) was carefully removed from each centrifuge tube with a sterile 10 ml pipette into as many sterile 40 ml conical centrifuge tubes. Any agitation of the tubes containing both sporulated and unsporulated oocysts disturbed their delicate separation and made necessary recentrifugation.

Each tube containing sterile sporulated oocysts was brought to 40 ml with sterile distilled water and then centrifuged (1000 rpm/10 min.). The supernatant was discarded and the sporulated oocysts were washed several times using sterile distilled water and aseptic techniques until no Clorox TM odor remained.

Clean sporulated oocysts were enumerated microscopically using a hemocytometer and stored at room temperature in sterile distilled water to which 125 mg Fungizone TM (GIBCO No. 529L) was added per 40 ml tube.

A tube containing sporulated oocysts, which had been stored not more than 3 months, was selected and sporocysts sedimented, if necessary, by centrifugation (1000 rpm/10 min.). All supernatant was decanted and oocysts resuspended in the remaining water, at a volume equal to $1-1.5\times$ that of the pelleted oocysts. Two or four milliliters of this suspension was aseptically removed into a sterile tissue grinder and homogenized for 7-10 minutes at maximum speed with care not to heat the suspension above body temperature.

A sample of the homogenate was examined microscopically to determine the extent of sporocyst liberation. If more than 10% of the oocysts remained intact, homogenation was continued until $\geq 90\%$ had released their sporocysts.

Suspensions containing $\geq 90\%$ sporocysts were placed in a sterile 40 ml conical centrifuge tube containing 20 ml of excystation fluid (19 ml 0.25% trypsin, 1 ml fresh sterile chicken bile) and the pH adjusted, if necessary, to 8.0 with sterile 7.5% sodium bicarbonate solution (GIBCO No. 508). The resulting mixture was incubated in a 37° C water batch with occasional hand shaking and periodic microscopic examination of samples for excystation.

If excystation was slow (<20% in 45 min.) 0.5 to 1.0 ml of bile was added and the solution readjusted to pH 8.0. When $\geq 90\%$ of the sporocysts had ruptured, sporozoites were harvested by centrifugation (1000 rpm/5 min.). The resulting supernatant was discarded, and sporozoites were suspended in 20 ml of Earl's Balanced Salt Solution (EBSS) containing 6.80 g/L NaCl, 0.40 g/L KCl, 0.20 g/L $CaCl_2$, 0.20 g/L $MgSO_4.7H_2O$, 0.14 g/L $NaH_2PO_4.H_2O$, 1.00 g/L Glucose, 2.20 g/L $NaHCO_3$, and 0.01 g/L Phenol Red supplemented with 0.2 ml of antibiotic solution containing penicillin-streptomycin, GIBCO No. 514 (10,000 units penicillin G, sodium and 100,000 µg streptomycin sulfate in normal saline. Stored at −20° C. This suspension was centrifuged at low speed (400 rpm/2-3 min.) to remove debris, and the resulting supernatant, which contained the sporozoites, carefully removed with a sterile pipette into a sterile tube.

A $1/10\times$ or $1/20\times$ dilution of these sporozoites was counted microscopically in a hemocytometer and the original solution then diluted to 200,000 sporozoites/ml with EBSS supplemented with antibiotic solution for immediate use as inoculum for tests.

Alternatively, sporozoites were diluted to 400,000-800,000/ml in EBSS plus antibiotics and stored at 3°-5° C for up to 48 hours before use. Such refrigerated suspensions were brought to room temperature, recounted and diluted to 200,000/ml just prior to use as inoculum.

For in vitro screen tests, Hubbard×Hubbard chicks were maintained on drug-free starter diets in brooders in a coccidia-free room. Water was available ad libitum. At 2-3 weeks of age, 3-6 chicks were sacrificed by decapitation and bled. All tissue culture preparation, propagation and test steps were carried out using strict aseptic techniques.

Kidneys were removed into a sterile 10 cm petri dish containing 15-20 ml of sterile EBSS without $CaCl_2$ or $MgSO_4.7H_2O$ (EBSS-Ca-Mg) which had been prewarmed to 39° C. Coagulated blood and connective tissue were removed with sterile forceps. Kidney pieces were washed 3-4 times with 39° C. EBSS-Ca-Mg and transferred to a sterile 250 ml trypsinizing flask containing a sterile magnetic stir bar and fitted with stainless steel closures.

The flask was placed on a stir plate and contents mixed slowly for 5 minutes. The buffer solution was carefully decanted and replaced with 35 ml of 0.25% trypsin solution GIBCO No. 505 (2.5 grams porcine parvovirus tested trypsin per liter HBSS without $CaCl_2$ or $MgSO_4.7H_2O$) at 39° C.

After 15 minutes of slow stirring, kidney pieces were allowed to settle and the liquid decanted as waste. Another 35 ml of trypsin solution at 39° C was added and stirred slowly with kidney pieces for 5 minutes. This time, after allowing small kidney particles to settle, the solution was decanted through a sterile funnel containing several layers of sterile cheesecloth into a sterile 40 ml conical centrifuge tube and held on ice.

Five-minute trypsinizations were repeated 2 or 3 times and filtrates were combined and held on ice. Kidney cells were sedimented from the filtrates by centrifugation (1000 rpm/10 min.) and the supernatant discarded.

Kidney cells then were grossly separated from underlying red blood cells by gentle agitation in 10-15 ml of cold EBSS. Kidney cells were pooled into two 40 ml sterile conical centrifuge tubes and dispersed by agitation. Tubes were brought to 40 ml with cold EBSS and centrifuged as before. The supernatant was replaced with 10 ml of growth medium 500 ml lactalbumin hydrolysate with Earle's salts (ELH) (same as EBSS with 6.5 g/liter lactalbumin hydrolysate added), 50 ml fetal calf serum and 6 ml antibiotic solution and kidney cells freed from remaining red blood cells by gentle agitation.

Kidney cells next were combined in a single sterile tube and evenly dispersed by agitation. An appropriate dilution (usually 1/10× to 1/25×) was counted microscopically in a hemocytometer and the cell suspension diluted in 500 ml sterile bottles to 200,000 to 250,000 cells/ml of growth medium.

Multiwell tissue culture plates (Falcon No. 3008 or Costar No. 3524) were employed in all in vitro screen tests. Immediately after preparation of the kidney cell suspension, each of the 24 wells of 20 to 60 multiwell plates was inoculated with 1 ml of cells using a sterile syringe-type continuous pipettor (Cornwall).

Plates then were incubated at once in a 5% $CO_2$ incubator at 39° C and ≧80% humidity. At about 24 hours one plate was removed and briefly examined for monolayer initiation under phase microscopy at 200×. At 40-48 hours monolayer growth was well initiated and satisfactory for initiation of drug tests. At this time attached cells were spreading and putting out arm-like projections in many areas of each well. The medium on plates which would not be used for drug tests at this time was replaced with prewarmed EBSS plus antibiotics, and these plates were returned to the incubator until time of use 24 to 48 hours later. The latter step was incorporated to remove debris and toxins from the young cell monolayers and also delay monolayer growth until initiation of drug tests.

For each test compound an estimated 10 mg of test compound was placed in a 15×150 mm disposable screw-cap test tube (Belco No. 2009-16150). In a typical test employing 25 multiwell plates, tubes containing test compounds were set up and four drops of dimethylsulfoxide (DMSO) were added to each tube. Next 10 ml sterile distilled water was added to each tube and the tubes were capped tightly and mixed by agitation. Primary compound solutions containing about 1000 ppm test compound were serially diluted in disposable tubes (Falcon No. 2051) containing ½ strength growth medium, to yield the concentrations shown in Table 3 below. Sterile 1 cc disposable syringes (Tomac) were employed both for making dilutions and adding test compounds to plates.

In setting up drug tests, five multiwell plates containing 48-96 hr monolayers were removed as a group from the incubator. The medium was quickly poured off one multiwell plate and 0.5 ml of the lowest dilution of test compound was added to each of two wells in the first column of wells, and an equal volume of a higher dilution of the same substance was added to the remaining two wells in the same column. This procedure was repeated with the next test substance using the wells in the second column on the plate. Dilutions of the remaining test substances were placed in corresponding columns of the plate.

After compounds had been added to the first set of five plates, 0.5 ml of a $2 \times 10^5$/ml suspension of sporozoites was added to each well of each plate using a sterile continuous pipettor. To minimize the effects of exposing growth medium to the atmosphere, all additions were made rapidly and inoculated plates were immediately returned to the incubator.

Three days after drug and sporozoite addition, plates were removed a few at a time from the incubator for enumeration of parasites. Statistical evaluation of the number and distribution of second generation schizonts in kidney cell monolayers indicated that counts of five fields needed to be made for each concentration of each test substance to detect with an 80% probability a compound producing 90% inhibition of the test parasite. The medium was quickly discarded and counts made under phase microscopy at 200× of the total numbers of schizonts and merozygotes per field in each of five random fields. The average number of parasites per field was then calculated.

The results of the in vitro anticoccidial tests, which are given in Table 3 below, show the compounds to have toxic effects upon cultured cells. Tests in which a compound totally inhibited monolayer growth or rendered the condition of the few attached cells so poor that parasite development could not be detected, if it were to occur, were scored as "toxic". Tests in which the monolayer exhibited some noticeable signs of chemical toxicity were counted but also noted as such.

TABLE 3

| Compound of Example | % Inhibition of Coccidia Concentration (ppm) | | | | | |
|---|---|---|---|---|---|---|
| | 100 | 10.0 | 1.0 | 0.1 | 0.01 | 0.001 |
| 1 | T | T | 98 | 61 | 67 | 53 |
| 2 | T | T | 100 | 89 | 71 | 42 |
| 3 | — | 98 | — | 88.6 | — | — |
| 5 | T | 100 | 31 | 6 | 0 | 1 |
| 6 | — | 100 | — | 60 | — | — |
| 8 | T | T | 99 | 12 | 9 | 0 |

T = toxic (inhibited kidney cell monolayer formation)

EXAMPLE 18

Using the procedures of Example 1 repeated in all essential details but substituting the appropriate starting materials, compounds having the structure shown in formula I above and which are effective in promoting growth and feed efficiency, and in controlling coccidiosis in poultry, are synthesized with the following substituents:

$R_1 =$ —Br, —CH$_3$, —C$_2$H$_5$, —C$_3$H$_7$, —C$_4$H$_9$, —C$_5$H$_{11}$, —OC$_2$H$_5$, —OC$_3$H$_7$, —OC$_4$H$_9$, —OC$_5$H$_{11}$.

$R_2 =$ —Br, —CH$_3$, —C$_2$H$_5$, —C$_3$H$_7$, —C$_4$H$_9$, —C$_5$H$_{11}$, —OC$_2$H$_5$, —OC$_3$H$_7$, —OC$_4$H$_9$, —OC$_5$H$_{11}$.

$R_3 =$ —OOCH$_3$, —OOC$_2$H$_5$, —OOC$_3$H$_7$, —OOC$_4$H$_9$, —OOC$_5$H$_{11}$, —OCOCH$_3$, —OCOC$_2$H$_5$, —OCOC$_3$H$_7$, —OCOC$_4$H$_9$, —OCOC$_5$H$_{11}$.

$R_3' =$ —OOCH$_3$, —OOC$_2$H$_5$, —OOC$_3$H$_7$, —OOC$_4$H$_9$, —OOC$_5$H$_{11}$, —OCOCH$_3$, —OCOC$_2$H$_5$, —OCOC$_3$H$_7$, —OCOC$_4$H$_9$, —OCOC$_5$H$_{11}$.

$R_4 =$ —Br, —C$_2$H$_5$, —C$_3$H$_7$, —C$_4$H$_9$, —C$_5$H$_{11}$, —OC$_2$H$_5$, —OC$_3$H$_7$, —OC$_4$H$_9$, —OC$_5$H$_{11}$, —OOCC$_2$H$_5$, —OOCC$_3$H$_7$, —OOCC$_4$H$_9$, —OOCC$_5$H$_{11}$.

$R_4' =$ —Br, —C$_2$H$_5$, —C$_3$H$_7$, —C$_4$H$_9$, —C$_5$H$_{11}$, —OC$_2$H$_5$, —OC$_3$H$_7$, —OC$_4$H$_9$, —OC$_5$H$_{11}$, —OOCC$_2$H$_5$, —OOCC$_3$H$_7$, —OOCC$_4$H$_9$, —OOCC$_5$H$_{11}$.

$R_5 =$ —Br, —C$_2$H$_5$, —C$_3$H$_7$, —C$_4$H$_9$, —C$_5$H$_{11}$, —OC$_2$H$_5$, —OC$_3$H$_7$, —OC$_4$H$_9$, —OC$_5$H$_{11}$, —OOCC$_2$H$_5$, —OOCC$_3$H$_7$, —OOCC$_4$H$_9$, —OOCC$_5$H$_{11}$.

$R_5' =$ —Br, —C$_2$H$_5$, —C$_3$H$_7$, —C$_4$H$_9$, —C$_5$H$_{11}$, —OC$_2$H$_5$, —OC$_3$H$_7$, —OC$_4$H$_9$, —OC$_5$H$_{11}$, —OOCC$_2$H$_5$, —OOCC$_3$H$_7$, —OOCC$_4$H$_9$, —OOCC$_5$H$_{11}$.

$R_6 =$ —Br, —C$_2$H$_5$, —C$_3$H$_7$, —C$_4$H$_9$, —C$_5$H$_{11}$, —OC$_2$H$_5$, —OC$_3$H$_7$, —OC$_4$H$_9$, —OC$_5$H$_{11}$, —OOCC$_2$H$_5$, —OOCC$_3$H$_7$, —OOCC$_4$H$_9$, —OOCC$_5$H$_{11}$.

$R_6' =$ —Br, —C$_2$H$_5$, —C$_3$H$_7$, —C$_4$H$_9$, —C$_5$H$_{11}$, —OC$_2$H$_5$, —OC$_3$H$_7$, —OC$_4$H$_9$, —OC$_5$H$_{11}$, —OOCC$_2$H$_5$, —OOCC$_3$H$_7$, —OOCC$_4$H$_9$, —OOCC$_5$H$_{11}$.

$R_7 =$ —OCCH$_3$, —OCC$_2$H$_5$, —OCC$_3$H$_7$, —OCC$_4$H$_9$, —OCC$_5$H$_{11}$.

We claim:

1. A method for producing a compound of the formula

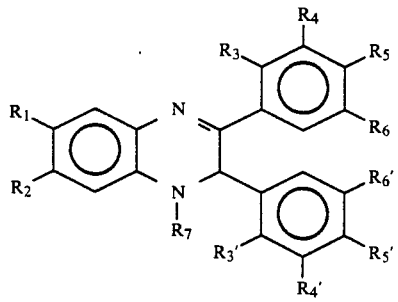

(I)

wherein R$_1$ and R$_2$ are independently selected from the group consisting of hydrogen, halogen, lower alkyl and lower alkoxy; R$_3$ and R$_3'$ are independently selected from the group consisting of halogen, hydroxy, lower alkoxy, lower acyloxy and lower alkylcarbonyloxy, R$_4$, R$_4'$, R$_5$, R$_5'$, R$_6$ and R$_6'$ are independently selected from the group consisting of hydrogen, halogen, hydroxy, lower alkyl, lower alkoxy and lower acyloxy; and R$_7$ is hydrogen or lower acyl; the method comprising:

(a) reacting a phenylenediamine derivative of the formula

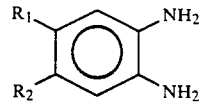

wherein R$_1$ and R$_2$ are as defined above, with a benzaldehyde derivative of the formula

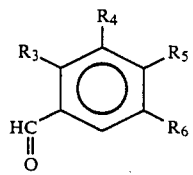

wherein R$_3$, R$_4$, R$_5$ and R$_6$ are as defined above, to form a dibenzylidene compound of the formula

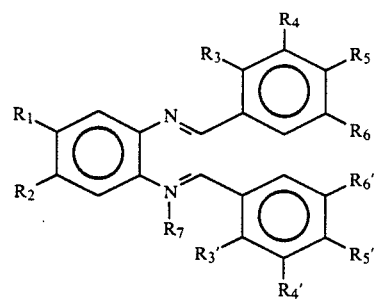

(b) treating the dibenzylidene compound produced in step (a) with sodium cyanide to produce a compound of the formula (I).

2. The method of claim 1 wherein the molar ratio of the phenylenediamine derivative to the benzaldehyde derivative is about 1:2, said derivatives are reacted at a temperature of about 50°-70° C, and said dibenzylidene compound is reacted in a molar excess of said sodium cyanide at a temperature of about 0°-30° C.

3. The method of claim 1, wherein R$_7$ is hydrogen.

4. The method of claim 3, wherein R$_1$ and R$_2$ are independently selected from the group consisting of hydrogen, chloro, bromo, lower alkyl and lower alkoxy; R$_3$ and R$_3'$ are independently selected from the group consisting of chloro, bromo, hydroxy, lower alkoxy and lower acyloxy and R$_4$, R$_4'$, R$_5$, R$_5'$, R$_6$ and R$_6'$ are independently selected from the group consisting of hydrogen, chloro, bromo, hydroxy, lower alkyl, lower alkoxy, and lower acyloxy.

5. The method of claim 4, wherein R$_1$ and R$_2$ are independently selected from the group consisting of hydrogen, chloro and methoxy; R$_3$ and R$_3'$ are independently selected from the group consisting of hydroxy, methoxy and acetoxy; and R$_4$, R$_4'$, R$_5$, R$_5'$, R$_6$ and R$_6'$ are independently selected from the group consisting of hydrogen, chloro, hydroxy, methyl, methoxy and acetoxy.

6. The method of claim 5, wherein R$_3$ and R$_3'$ are each hydroxy.

7. The method of claim 5 or 6 wherein R$_1$ and R$_2$ are each chloro.

8. The method of claim 7, wherein R$_4$, R$_4'$, R$_5$ and R$_5'$ are each hydrogen and R$_6$ and R$_6'$ are chloro.

* * * * *